(12) United States Patent
Lin et al.

(10) Patent No.: US 6,248,923 B1
(45) Date of Patent: Jun. 19, 2001

(54) PROCESS FOR THE PRODUCTION OF FLUOROCARBOXYLIC ACID ANHYDRIDES

(75) Inventors: Robert Lin, Kingsport; Robert Thomas Hembre, Johnson City; Edwin Franklin Holcombe, III, Morristown; Mark Robert Shelton, Kingsport, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/520,526

(22) Filed: Mar. 8, 2000

Related U.S. Application Data

(60) Provisional application No. 60/152,290, filed on Sep. 3, 1999.

(51) Int. Cl.[7] .................................................. C07C 51/54
(52) U.S. Cl. ............................................................ 562/892
(58) Field of Search ............................................. 562/892

(56) References Cited

U.S. PATENT DOCUMENTS 4,595,541 * 6/1986 Amiet et al. .

FOREIGN PATENT DOCUMENTS 45-038-523    12/1970 (JP) .

OTHER PUBLICATIONS

J. M. Tedder, Chem. Rev., 1955, 55, pp 787–827.
Swarts, Bull. Sci. Acad. Roy. Belg., 1922, 8, pp 342–70.
E. J. Bourne et al, J. Chem. Soc., 1954, 2006–2012.
Reginald F. Clark et al, J. Am. Chem. Soc., 1953, 75, 6305–06.

Blake et al, J. Chem. Soc., (B), Perkin Transactions II, 1976, pp 1533–36.

Nagayama et al, Bull. Chem. Soc. Jpn., 1999, 72, 799–803.

Ferris et al, J. Am. Chem. Soc., 1953, 75, 232–33.

* cited by examiner

*Primary Examiner*—Paul J. Killos
*Assistant Examiner*—John N. Calve
(74) *Attorney, Agent, or Firm*—Michael J. Blake; Harry James Gwinnell

(57) ABSTRACT

Disclosed is process for the production of symmetrical fluoro-substituted anhydrides from mixed or unsymmetrical anhydrides, i.e., wherein the two carboxylic acid acyl groups of the anhydrides are different, by subjecting an unsymmetrical anhydrides to reactive distillation to produce a lower boiling product comprising a symmetrical fluorocarboxylic acid anhydride and a higher boiling product comprising a second symmetrical anhydride. The process is particularly useful for the coproduction of trifluoroacetic anhydride (TFAA) and acetic anhydride ($Ac_2O$) from ketene and trifluoroacetic acid wherein ketene and trifluoroacetic acid (TFA) are reacted to produce a mixed anhydride, acetyl trifluoroacetate (Ac-TFA), which then is subjected to reactive distillation to produce a vapor product comprising TFAA and a liquid product comprising $Ac_2O$.

19 Claims, No Drawings

PROCESS FOR THE PRODUCTION OF FLUOROCARBOXYLIC ACID ANHYDRIDES

CROSS REFERENCE TO RELATED APPLICATION

This application claims the benefit of U.S. Provisional Application No. 60/152,290, filed Sep. 3, 1999.

INTRODUCTION

This invention pertains to a novel process for the production of certain fluoro-substituted carboxylic acid anhydrides which are symmetrical, i.e., wherein the two carboxylic acid acyl groups of the anhydrides are the same. More specifically, this invention pertains to a process for the preparation of symmetrical fluoro-substituted anhydrides from mixed or unsymmetrical anhydrides, i.e., wherein the two carboxylic acid acyl groups of the anhydrides are different, by subjecting an unsymmetrical anhydride to reactive distillation to produce a lower boiling product comprising a symmetrical fluorocarboxylic acid anhydride and a higher boiling product comprising a second symmetrical anhydride. In accordance with a preferred embodiment, the present invention pertains to a process wherein ketene and trifluoroacetic acid (TFA) are reacted to produce a mixed anhydride, acetyl trifluoroacetate (Ac-TFA), which then is subjected to reactive distillation to produce a vapor product comprising TFM and a liquid product comprising $Ac_2O$.

BACKGROUND OF THE INVENTION

Various processes for the preparation of carboxylic acid anhydrides are known. For example, acetic anhydride, the most common anhydride, may be prepared from acetic acid by the steps of (1) cracking or pyrolyzing acetic acid to produce ketene and (2) reacting the ketene with acetic acid to produce acetic anhydride. Higher molecular weight carboxylic acid anhydrides, e.g., substituted anhydrides and/or anhydrides which contain more than 4 carbon atoms, typically are prepared by contacting the corresponding carboxylic acid with acetic anhydride, e.g., butyric anhydride may be prepared by contacting butyric acid with acetic anhydride.

Trifluoroacetic anhydride (TFAA) is a strong dehydrating agent and has a broad range of chemical reactivity including the activation of carboxylic acids as mixed anhydrides (J. M. Tedder Chem. Rev. 1955, 55, 787–827). TFAA is a useful chemical in the synthesis of polymers and fine chemicals. However, it is expensive and, thus, more efficient methods for its synthesis are desirable. Because TFAA is a very reactive anhydride, a strong desiccant is required for its preparation. It was first prepared by Swarts in 1922 (*Bull. Sci. Acad. Roy. Belg.* 1922, 8, 343–70) by the dehydration of TFA using phosphorus pentoxide. This method is convenient for small-scale TFAA synthesis but too inefficient for large-scale production. Phosphorus pentoxide is a water-sensitive solid that is difficult to work with on a large scale. Its cost and the expenses associated with the large amount of phosphate-containing waste it generates are strong disadvantages. In addition, minimizing manufacturing costs by minimizing waste is highly desirable.

The use of sulfur trioxide as the desiccant is an improvement over phosphorus pentoxide in this respect. TFM can be produced by the reaction of trifluoroacetyl chloride and sodium trifluoroacetate with the coproduction of sodium chloride which is less difficult to dispose of than is phosphoric acid or sulfuric acid resulting from the phosphorus pentoxide and sulfur trioxide processes. However, the cost of producing trifluoroacetyl chloride limits the feasibility of this method.

In 1954, E. J. Bourne and coworkers, *J. Chem. Soc.* 1954, 2006–12, showed that at equilibrium the reaction of acetic anhydride and TFA to produce Ac-TFA and the reaction of Ac-TFA and TFA to produce TFM are not favorable. Nonetheless, the production of TFAA by reacting $Ac_2O$ with TFA is described in U.S. Pat. No. 4,595,541 which discloses a process for the preparation of TFAA by contacting TFA with the anhydride of acetic or an α-halogenated carboxylic acid. Thus, contacting TFA (8 molar equivalents) with acetic, mono-, di- or tri-chloroacetic anhydrides produces TFAA in yields of 36, 59, 67 and 74%, respectively, and the conclusion that anhydride-based processes using a-chlorinated acetic anhydrides are preferred for the synthesis of TFAA. A process that produces TFAA in high yields from inexpensive raw materials and generates little or no waste which presents disposal problems, e.g., only water or marketable byproducts, is thus highly desirable. The present invention provides such a process.

BRIEF SUMMARY OF THE INVENTION

We have developed a process for the production of two symmetrical carboxylic acid anhydrides, i.e., anhydrides composed of two identical, carboxylic acid acyl groups, by first forming mixed or unsymmetrical anhydrides, i.e., anhydrides composed of two different carboxylic acid acyl groups, and then subjecting the unsymmetrical anhydrides to reactive distillation to produce a lower boiling product comprising a first symmetrical fluorocarboxylic acid anhydride and a higher boiling product comprising a second symmetrical anhydride.

One embodiment of our invention, therefore, concerns a process for the production of a first, symmetrical, fluorocarboxylic acid anhydride and acetic anhydride as a second symmetrical, carboxylic acid anhydride which comprises contacting ketene and a fluorocarboxylic acid having 2 to 4 carbon atoms to produce an acetyl mixed anhydride and subjecting the acetyl mixed anhydride to reactive distillation to produce a lower boiling product comprising the symmetrical fluorocarboxylic acid anhydride and a higher boiling product comprising acetic anhydride ($Ac_2O$), provided that (i) the boiling point of the symmetrical fluorocarboxylic anhydride is lower than the boiling point of the fluorocarboxylic acid and (ii) the boiling point of the symmetrical fluorocarboxylic anhydride is lower than the boiling point of acetic anhydride.

A second and especially preferred embodiment of the present invention concerns a process for the production of TFAA using ketene and TFA as the raw materials which is suitable for continuous operation to produce commercial quantities of TFAA. This second embodiment concerning the production of TFAA comprises contacting ketene and TFA to produce a mixed anhydride, Ac-TFA, which then is subjected to reactive distillation to produce a highly volatile product comprising TFAA and a liquid product comprising $Ac_2O$. In contrast to the known TFAA syntheses described above, the only byproduct of our novel process is acetic anhydride which represents an economic advantage rather than a burden.

A third embodiment of the invention pertains to a process for the coproduction of trifluoroacetic anhydride (TFAA) and a carboxylic anhydride having the formula [R—C(O)]$_2$O which comprises the steps of: preparing a mixed anhydride having the formula R—C(O)—O—(O)-CF$_3$ and subjecting the mixed anhydride to reactive distillation wherein the mixed anhydride disproportionates to produce a lower boiling product comprising TFM and a higher boiling product comprising an anhydride having the formula $[R-C(O)]_2O$; wherein R is a hydrocarbyl group containing up to about 6 carbon atoms.

DETAILED DESCRIPTION

The process of the present invention engages the disproportionation of a mixed anhydride derived from a carboxylic acid ($R-C(O)OH$) and a fluorinated carboxylic acid ($R_F-C(O)OH$) to yield the corresponding symmetric anhydrides.

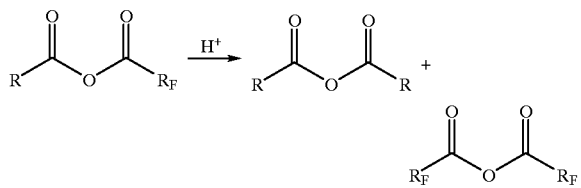

This disproportionation is carried out via a novel reactive distillation. Reactive distillations that convert one symmetric anhydride to another are well known. For instance, acetic anhydride ($Ac_2O$) can be used to convert propionic acid (PrOH) to its anhydride ($Pr_2O$) in a reactive distillation. In order for such a process to operate in an ideal and continuous fashion the two products, AcOH and $Pr_2O$ must be the lowest and highest boiling constituents of the mixture equilibrating in the length of the distillation column.

$$2\ PrOH + Ac_2O \longrightarrow 2\ AcOH + Pr_2O$$
b.p. (° C.) =    141    140              117    167

For the process of the invention proposed herein a reactant mixed anhydride is disproportionated to yield two symmetric anhydrides. As above, in order for such a process to operate in an ideal fashion the mixed anhydride must have a boiling point intermediate between the two symmetric anhydrides, as shown below for acetyl trifluoroacetate (Ac-TFA).

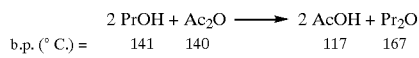
acetyl trifluoroacetate (Ac-TFA)

$$2\ \text{Ac-TFA} \xrightarrow{H^+} \text{TFAA} + Ac_2O$$
b.p. (° C.) =    95              40    140

This is in general the case for mixed anhydrides. However, because the two carboxylic acids which are constituents of the mixed anhydride are intermediates in its disproportionation it is ideal if they too have boiling points that are between those of the symmetric anhydrides in order for the reactive distillation to operate properly.

Table 1 shows that carboxylic anhydrides, as a rule, have higher boiling points than their corresponding acids. It is thus necessary that one of the anhydrides produced in the process of the present invention be anomalous, i.e. it must have a lower boiling point than its corresponding acid. The anhydrides of the lower fluorinated carboxylic acids exemplify this anomaly. As a result, the mixed anhydrides of these acids are appropriate as reactants for disproportionation by reactive distillation. Examples of fluorinated carboxylic acids from which the residue $R_F-C(O)-$ may be derived are trifluoroacetic, pentafluoropropionic and heptafluorobutyric acids. The most preferred mixed anhydrides are those derived from trifluoroacetic acid.

TABLE 1

Boiling Points (° C.) of Selected Carboxylic Acids and Anhydrides.

| R | R—C(O)OH | R—C(O)—O—C(O)—R |
|---|---|---|
| $CH_3-$ | 116 | 140 |
| $C_2H_5-$ | 141 | 167 |
| $C_3H_7-$ | 162 | 199 |
| $CF_3-$ | 72 | 40[a] |
| $C_2F_5-$ | 96 | 72[a] |
| $C_3F_7-$ | 120 | 107[a] |
| $C_4F_9-$ | 140 | 137[a] |

[a]Reginald F. Clark and J. H. Simons J. Am. Chem. Soc. 1953, 75, 6305.

In accordance with the most preferred embodiment of the present invention, TFA and ketene are reacted according to known procedures, e.g., see Blake, et al., *J. Chem. Soc.*,(B) 1976, 1533–36, to produce the mixed anhydride Ac-TFA. This reaction may be carried out at a temperature in the range of about −76 to 70° C., preferably about −20 to 40° C. The mole ratio of TFA:ketene may be in the range of about 100:1 to 0.75:1, preferably about 10:1 to 0.9:1. A solvent such as a chlorinated hydrocarbon, e.g., dichloro-methane and o-dichlorobenzene; an ether, e.g., tetrahydrofuran and dialkyl ethers; and hydrocarbons, e.g., benzene and toluene; may be used but normally is not preferred. Pressure is not an important feature of the TFA-ketene reaction which normally is carried out at ambient pressure although low pressure or moderately above ambient pressure may be used.

Other methods for the synthesis of mixed anhydrides such as Ac-TFA are known. For example, Ac-TFA may be prepared by the carbonylation of methyl trifluoroacetate catalyzed by transition metals in a manner analogous to that reported for carbonylation of benzyl trifluoroacetate, e.g., see Yamamoto, et al. *Bull. Chem. Soc. Jpn.* 1999, 72, 799–803. Likewise, reaction of trifluoroacetyl chloride with either acetic acid or salts of acetic acid may produce Ac-TFA by a method similar to that described in Japanese Patent 45-038-523. Reaction of acetyl chloride with trifluoroacetic acid or salts of trifluoroacetic acid also has been demonstrated by Ferris and Emmons (*J. Am. Chem. Soc.* 1953, 75, 232–33). These methods are not preferred for large-scale synthesis, but, in principle, may be used to generate mixed anhydrides for processes that include their disproportionation as described below. The invention described herein does not exclude such alternatives but incorporates them as general methods secondary to the preferred reaction of ketene with TFA.

The preferred mixed anhydride Ac-TFA derived from TFA and ketene is subjected to reactive distillation, typically in a reactive distillation column equipped with trays, plates and/or packing material, wherein the mixed anhydride is disproportionated to TFM and $Ac_2O$. Such a disproportionation of a mixed anhydride of acetic acid is applicable to the production of any anhydride with a normal boiling point that is both about 20° C. less than that of $Ac_2O$ (i.e. <120° C.) and less than that of its corresponding acid. In addition to TFM, perfluoropropionic and perfluorobutyric anhydrides are examples that fulfill these requirements. The process of the present invention is directed to production of anhydrides which meet the above normal boiling point criteria and is not exclusive, for example, of the production of perfluoropropionic and perfluorobutyric anhydrides.

Although not essential, it is preferred to carry out the disproportionation of mixed anhydride Ac-TFA in the presence of TFA. When TFA is employed, the TFA:Ac-TFA mole ratio may be in the range of about 0.01:1 to 10:1, preferably about 0.1:1 to 3:1. The disproportionation may be carried out in the presence of strong acids in place of or in addition to excess TFA. Examples of such strong acids include sulfuric acid and polymeric resins containing acidic functional groups, e.g., polymer-bound sulfonic acids such as those derived from vinylbenzenesulfonic acid and divinylbenzene. The acidic polymeric resins, e.g., ion exchange resins such as those sold under the tradenames Nafion and Duolite, may be introduced into the distillation apparatus and/or incorporated into the distillation apparatus.

The reactive distillation column is operated at temperatures between the boiling points of the two symmetric anhydrides being produced at the pressure at which the column is operated. For the production of TFAA and $Ac_2O$ at ambient pressure, the range is about 40 to 150° C. Typically, the temperature at the bottom or base of the reactive distillation column is in the range of about 110 to 150° C. and the temperature at the top or head of the column is in the range of about 35 to 70° C. Column head temperatures in the range of about 38 to 45° C. and column base temperatures in the range of about 120 to 145° C. are preferred. The pressure within the column is not important and thus pressure moderately above or below ambient pressure may be used although the reactive distillation normally is operated at ambient pressure or pressures slightly above ambient. For example, the use of reduced pressure is not preferred because such would make the condensation of the low boiling TFAA more difficult. Operation of the reactive distillation column at elevated pressure may be preferred to make the condensation easier. The reactive distillation uses a column with plates and/or trays and/or packing that cause numerous equilibrations to achieve total disproportionation.

The process of the present invention may be operated in a batch, continuous or semi-continuous manner. For example, the process may be carried out by first reacting ketene and TFA in a reaction vessel equipped with a distillation column to form the mixed anhydride Ac-TFA. The vessel containing the Ac-TFA then may be heated to effect reactive distillation of the contents of the reaction vessel and recover TFAA from the upper section of the distillation column. The process for the coproduction of TFAA and $Ac_2O$ preferably is carried out in a continuous or semi-continuous manner comprising the steps of: (1) introducing ketene and TFA to a reaction vessel wherein the ketene and TFA react to form a product comprising Ac-TFA; (2) removing product from the reaction vessel and introducing it into the mid-section of a reactive distillation column wherein the Ac-TFA disproportionates to form TFAA and $Ac_2O$; (3) removing a lower boiling product comprising TFAA from the upper section of the reactive distillation column; and (4) removing a higher boiling product comprising $Ac_2O$ from the lower section of the reactive distillation column. An alternative mode of continuous or semi-continuous operation of the process, which may be but is not necessarily used in conjunction with the first aspect of the invention, comprises the steps of (1) introducing ketene and TFA directly into a reactive distillation column wherein the ketene and TFA react to form Ac-TFA which disproportionates to form TFAA and $Ac_2O$; (2) removing a lower boiling product comprising TFAA from the upper section of the reactive distillation column; and (3) removing a higher boiling product comprising $Ac_2O$ from the lower section of the reactive distillation column.

The Ac-TFA produced by the reaction of ketene and TFA alternatively may be distilled at low temperature to avoid its disproportionation and provide a purified Ac-TFA. To produce a purified Ac-TFA the distillation temperature must be less than about 50° C., e.g., 20 to 45° C. This requirement is illustrated by Bourne, et al. (loc.cit.) who report a 97% yield of Ac-TFA upon combining equimolar amounts of $Ac_2O$ with TFM, but only a 60% yield of Ac-TFA upon distillation at 95° C. Back-reaction of Ac-TFA (disproportionation) reduces their isolated yield. Disproportionation may be avoided and essentially quantitative distillation achieved at temperatures of approximately 25° C. Because the reaction of a slight excess of ketene with TFA can be carried out at such low temperatures, a unique high-yield process for the production of Ac-TFA is obtained if the so-produced Ac-TFA is distilled at pressures less than about 0.5 bar absolute, and preferably less than 0.1 bar absolute.

Mixed anhydrides of TFA and other carboxylic acids, i.e., carboxylic acids other than acetic acid, also may be used as the feed material to the reactive distillation procedure described above. Examples of such mixed anhydrides include those having the general formula RC(O)-TFA wherein R is an alkyl, alkenyl, cycloalkyl, or aryl, including both carbocyclic and heterocyclic aryl, of up to about 6 carbon atoms. The R group is limited by the need for the normal boiling point of the RC(O)-TFA mixed anhydride to be less than about 200° C., preferably less than 150° C. Examples of carboxylic acids from which residue R—C(O)— may be derived include (in addition to acetic) propionic, n- and i-butyric cyclopropanecarboxylic, acrylic, benzoic and furfurylic acids. A broader aspect of our invention therefore comprises a process for the coproduction of trifluoroacetic anhydride (TFAA) and a carboxylic anhydride having the formula $[R-C(O)]_2O$ which comprises the steps of: (1) preparing a mixed anhydride having the formula $R-C(O)-O-(O)-CF_3$ in a reaction vessel; (2) removing the mixed anhydride from the reaction vessel and introducing it into the mid-section of a reactive distillation column wherein the mixed anhydride disproportionates to form TFM and $[R-C(O)]_2O$; (3) removing a lower boiling product comprising TFAA from the upper section of the reactive distillation column; and (4) removing a higher boiling product comprising $[R-C(O)]_2O$ from the lower section of the reactive distillation column; wherein R is an alkyl, alkenyl, cycloalkyl or aryl group containing up to about 6 carbon atoms.

EXAMPLES

The process provided by the present invention is further illustrated by the following examples. As in the text above, abbreviations are used for trifluoroacetic acid (TFA), trifluoroacetic anhydride (TFAA), acetic anhydride ($Ac_2O$) and acetyl trifluoroacetate (Ac-TFA).

TFA and TFM were obtained from Mallinckrodt and Halocarbon Products, acetic acid and anhydride from J. T. Baker and diketene from Aldrich Chemical. Ketene was prepared by two methods: Method A: Diketene was passed through a heated tube at a temperature between 500–600° C. The formed gas was condensed in a dry ice bath at −78° C., redistilled into a calibrated cold finger, measured based on a density of 0.65 g/ml and transferred under reduced pressure to a reaction vessel also chilled to −78° C. Method B: Acetic acid was passed through a heated tube with quartz packing at a temperature between 500–600° C. The formed gas was trapped in a series of scrubbers through which TFA was circulated at a rate approximately 4.5 ml per minute. The TFA solution of Ac-TFA obtained from the scrubbers was characterized by $^{13}$C NMR to determine the relative amounts of acetic acid, acetic anhydride, acetyl trifluoroacetate and trifluoroacetic anhydride.

NMR spectra were obtained either on a Varian Gemini 300 NMR spectrometer or a Bruker DRX-500 NMR spectrometer with samples dissolved in CDCl$_3$, unless otherwise indicated. Chemical shifts (δ) are referenced to residual protons in CDCl$_3$ at 7.27 ppm and the carbon signal of CDCl$_3$ at 77.23 ppm. IR spectra were obtained on a Nicolet Impact 410 FT IR spectrometer and are referenced to the polystyrene aromatic band at 1601 cm$^{-1}$. Trace contents of acetyl moieties in samples of TFM or trifluoroacetyl moieties in samples of Ac$_2$O were quantified by hydrolysis/capillary electrophoresis using a Beckman-Coulter P/ACE MDQ capillary electrophoresis unit with indirect UV detection using λ=240 nm.

Example 1

Acetyl trifluoroacetate was prepared by the method of Bourne in which equimolar amounts of Ac$_2$O and TFAA are combined and heated to reflux for an hour, then fractionally distilled and the material boiling between 90–100° C. collected and characterized by IR and NMR: $^1$H NMR (CDCl$_3$): δ 2.39 ppm; $^{13}$C NMR (CDCl$_3$): δ 162.7,158.7 (q, $J_{CF}$=44.7 Hz), 113.9 (q, $J_{CF}$=286.3 Hz), 22.0 ppm; IR (CH$_2$Cl$_2$) $V_{C=O}$=1854,1782; $v_{C-O-C}$=1075 cm$^{-1}$.

Example 2

Ketene generated by Method A (0.8 ml, 12.3 mmol) was transferred to 100 mL of dichloromethane under vacuum and the solution was placed under an atmosphere of argon. An initial sample of the solution was assayed by IR showing the characteristic carbonyl absorption of ketene at 2133 cm$^{-1}$. Trifluoroacetic acid (0.3 ml, 3.9 mmol) was added via syringe to the ketene/dichloromethane solution. IR assay shows no TFA ($v_{C=O}$=1804 and 1784 cm$^{-1}$), only a mixture of ketene and Ac-TFA. Two additional aliquots of TFA converted all of the ketene to Ac-TFA (95% spectroscopic yield) without production of diketene ($v_{C=O}$=1895, 1862, 1744 and 1691 cm$^{-1}$), TFAA ($v_{C=O}$=1874, 1805 cm$^{-1}$) or any byproducts derived from the reaction of diketene with TFA. If desired, the Ac-TFA mixed anhydride (b.p. 95° C.) may be separated from the methylene chloride (b.p. 40° C.) by distillation.

Example 3

Ac-TFA (9.70 g) was placed in a 25 mL vial with a Teflon valve and attached to a Y-tube with a second 25 ml vial on a vacuum line manifold. The liquid was freeze-pump-thawed three times and then transferred at ambient temperature under a static vacuum of 0.1 torr from the initial vial to the second vial via condensation with liquid nitrogen. Upon thawing, 9.72 g (100% yield) of water white liquid with an IR spectrum identical to the starting material was obtained.

Example 4

Ac-TFA (156 g), TFA (10 g) and boiling chips were placed in a 500-mL, three-neck flask attached to a ten-plate Oldershaw trayed distillation column with a water-cooled condenser, under nitrogen. The distillation pot was heated (via a heating mantle) until the reflux observed at the head of the column was 38° C. At this point the distillation pot temperature was 80° C. Aliquots of distillate (10 mL) were removed at a reflux ratio of 0.75 over a period of 14 hours and assayed by IR spectroscopy to determine their composition. A total of 112.15 g of TFAA/TFA were collected, corresponding to a yield of TFAA greater than 85% (89.5 g TFAA). The base pot contained 52.4 g of liquid determined to be a mixture of acetic anhydride, Ac-TFA and acetic acid. A mass balance of 92% was accounted for by these products.

Comparative Example 1

Ac$_2$O (25.6 g, 0.25 moles), TFA (229.0 g, 2.0 moles) and boiling chips were placed in a 500-mL, three-neck flask attached to a five-plate Oldershaw trayed distillation column with a water-cooled condenser, under nitrogen. The distillation pot was heated (via a heating mantle) until the reflux observed at the head of the column was 49° C. at a reflux ratio of 2. At this point the distillation pot temperature was 82° C. The temperature overhead rose to 65° C. and the reflux ratio was adjusted to 10 prior to the withdrawal of aliquots of distillate (7–15 mL) over a period of 9.5 hours. These were assayed as described above to determine their composition. A total of 23.0 g of TFAA were collected (44±3% yield). The base pot contained 151.1 g of liquid determined to be a mixture of TFA and Ac-TFA. A mass balance of 95% was accounted for by these products.

Comparative Example 2

Ac$_2$O (51.1 g, 0.5 moles), TFA (114.1 g, 1.0 moles) and boiling chips were placed in a 500-mL, three-neck flask attached to a five-plate Oldershaw trayed distillation column with a water-cooled condenser, under nitrogen. The distillation pot was heated until the reflux observed at the head of the column was 46° C. At this point the distillation pot temperature was 101.4° C. Aliquots of distillate were removed at a reflux ratio of 9 (2–10 mL) over a period of five hours. These were assayed as above to determine their composition. A total of 16.2 g of TFM were collected (15.5±1% yield). The base pot contained 126.0 g of liquid determined to be a mixture of TFA and Ac-TFA. A mass balance of 96% was accounted for by these products.

Example 5

An acetyl trifluoroacetate (Ac-TFA, 18.59 kg) was synthesized by contacting ketene vapor with TFA (Method B). $^{13}$C NMR analyses showed this solution to be comprised of approximately 2.3% acetic acid, 7.5% acetic anhydride, 45.0% acetyl trifluoroacetate, 44.5% TFA and 0.7% TFM.

The Ac-TFA solution was continuously pumped at a rate of approximately 1.8 ml per minute into a 2.54 cm (1 inch) diameter distillation column packed with 1.52 meters (60 inches) of 4.1 mm (0.16 inch) Pro-Pak® protruded metal distillation packing over a period of 150 hours. The solution was fractionally distilled at a liquid reflux ratio varying between 0.6 and 0.9. Analysis of distillation column underflow samples showed the ratio of trifluoroacetyl (CF$_3$CO—) acid moieties to acetyl (CH$_3$CO) acid moieties to be approximately 0.040: 1. Analysis of distillation column distillate samples by capillary zone electrophoresis showed no detectable acetyl moieties. Likewise, analysis of column bottoms showed very low concentration of trifluoroacetyl moieties (<4 mole %). Overall conversion of acetyl trifluoroacetate to acetic anhydride and trifluoroacetic anhydride was found be 96%.

The invention has been described in detail with particular reference to preferred embodiments thereof, but it will be understood that variations and modifications can be effected within the spirit and scope of the invention.

We claim:

1. Process for the coproduction of a symmetrical fluorocarboxylic acid anhydride and acetic anhydride which comprises contacting ketene and a fluorocarboxylic acid containing 2 to 4 carbon atoms to produce an acetyl mixed anhydride and subjecting the acetyl mixed anhydride to reactive distillation to produce a lower boiling product comprising the symmetrical fluorocarboxylic acid anhydride and a higher boiling product comprising acetic anhydride ($Ac_2O$), provided that (i) the boiling point of the symmetrical anhydride of the fluorocarboxylic acid is lower than the boiling point of the fluorocarboxylic acid and (ii) the boiling point of the symmetrical anhydride of the fluorocarboxylic acid is lower than the boiling point of acetic anhydride.

2. Process according to claim 1 wherein the symmetrical anhydride of the fluorocarboxylic acid is selected from trifluoroacetic, pentafluoropropionic or heptafluorobutyric anhydrides.

3. Process according to claim 1 wherein the symmetrical anhydride of the fluorocarboxylic acid is trifluoroacetic anhydride (TFAA).

4. Process for the production of trifluoroacetic anhydride (TFAA) which comprises contacting ketene and trifluoroacetic acid (TFA) to produce a mixed anhydride, acetyl trifluoroacetate (Ac-TFA) and subjecting the mixed anhydride to reactive distillation to produce a lower boiling product comprising TFAA and a higher boiling product comprising acetic anhydride ($AC_2O$).

5. Process according to claim 4 wherein ketene and TFA are contacted at a temperature of about −20 to 40° C. and the mole ratio of TFA:ketene is in the range of about 10:1 to 0.9:1.

6. Process according to claim 5 wherein the reactive distillation is carried out in a distillation column operated at a head temperature in the range of about 35 to 70° C. and a column base temperature of about 110 to 150° C.

7. Process according to claim 6 wherein the reactive distillation is carried out in the presence of TFA in an amount which gives a TFA:Ac-TFA mole ratio in the range of about 0.1:1 to 3:1.

8. Process for the coproduction of trifluoroacetic anhydride (TFAA) and acetic anhydride ($Ac_2O$) which comprises the steps of: (1) introducing ketene and trifluoroacetic acid (TFA) into a reaction vessel wherein the ketene and TFA react to form a product comprising a mixed anhydride, acetyl trifluoroacetate (Ac-TFA); (2) removing product from the reaction vessel and introducing it into the mid-section of a reactive distillation column wherein the Ac-TFA disproportionates to form TFAA and $Ac_2O$; (3) removing a lower boiling product comprising TFM from the upper section of the reactive distillation column; and (4) removing a higher boiling product comprising $Ac_2O$ from the lower section of the reactive distillation column.

9. Process according to claim 8 wherein ketene and TFA are contacted at a temperature of about −20 to 40° C. and the mole ratio of TFA:ketene is in the range of about 10:1 to 0.9:1.

10. Process according to claim 9 wherein the reactive distillation is carried out at a column head temperature in the range of about 35 to 70° C. and a column base temperature of about 110 to 150° C.

11. Process according to claim 10 wherein the reactive distillation is carried out in the presence of TFA in an amount which gives a TFA:Ac-TFA mole ratio in the range of about 0.1:1 to 3:1.

12. Process for the coproduction of trifluoroacetic anhydride (TFAA) and acetic anhydride ($Ac_2O$) which comprises the steps of (1) introducing ketene and TFA into the mid-section of a reactive distillation column wherein the ketene and TFA react to form Ac-TFA which disproportionates to form TFM and $Ac_2O$; (2) removing a lower boiling product comprising TFAA from the upper section of the reactive distillation column; and (3) removing a higher boiling product comprising $Ac_2O$ from the lower section of the reactive distillation column.

13. Process according to claim 12 wherein the reactive distillation is operated at a column head temperature in the range of about 35 to 70° C. and a column base temperature of about 110 to 150° C.

14. Process according to claim 13 wherein the reactive distillation is carried out in the presence of TFA in an amount which gives a TFA:Ac-TFA mole ratio in the range of about 0.1:1 to 3:1.

15. Process for the coproduction of trifluoroacetic anhydride (TFM) and a carboxylic anhydride having the formula $[R—C(O)]_2O$ which comprises the steps of: (1) preparing a mixed anhydride having the formula R—C(O)—O—(O)—$CF_3$ in a reaction vessel; (2) removing the mixed anhydride from the reaction vessel and introducing it into the mid-section of a reactive distillation column wherein the mixed anhydride disproportionates to form TFM and $[R—C(O)]_2O$; (3) removing a lower boiling product comprising TFAA from the upper section of the reactive distillation column; and (4) removing a higher boiling product comprising $[R—C(O)]_2O$ from the lower section of the reactive distillation column; wherein R is an alkyl, alkenyl, cycloalkyl or aryl group containing up to about 6 carbon atoms.

16. Process according to claim 15 wherein the reactive distillation is carried out at a column head temperature in the range of about 35 to 70° C. and a column base temperature of about 160 to 220° C. and in the presence of TFA in an amount which gives a TFA:mixed anhydride mole ratio in the range of about 0.1:1 to 3:1.

17. Process according to claim 16 wherein step (1) comprises the reaction of carbon monoxide with an ester of trifluoroacetic acid wherein the ester contains less than about 8 carbon atoms.

18. Process according to claim 16 wherein step (1) comprises the reaction of trifluoroacetyl chloride with a carboxylic acid or a salt of a carboxylic acid containing less than about 6 carbon atoms.

19. Process according to claim 16 wherein step (1) comprises the reaction of a carboxylic acid chloride containing less than about 6 carbon atoms with trifluoroacetic acid or a salt of trifluoroacetic acid.

* * * * *

UNITED STATES PATENT AND TRADEMARK OFFICE
CERTIFICATE OF CORRECTION

PATENT NO. : 6,248,923 B1
DATED : June 19, 2001
INVENTOR(S) : Lin et al.

Page 1 of 1

It is certified that error appears in the above-identified patent and that said Letters Patent is hereby corrected as shown below:

Column 9, claim 8,
Line 50, "TFM" should be -- TFAA --.

Column 10, claim 12,
Line 12, "TFM" should read -- TFAA --.

Column 10, claim 15,
Lines 27 and 33, "TFM" should be -- TFAA --.

Signed and Sealed this

Fifteenth Day of January, 2002

Attest:

JAMES E. ROGAN
*Attesting Officer*     *Director of the United States Patent and Trademark Office*